United States Patent [19]
Behre et al.

[11] Patent Number: 6,093,852
[45] Date of Patent: Jul. 25, 2000

[54] PROCESS FOR PREPARING 4,6-DIAMINO-RESORCINOL DIHYDROCHLORIDE

[75] Inventors: Horst Behre, Odenthal; Helmut Fiege, Leverkusen; Heinz Ulrich Blank, Odenthal; Wolfgang Eymann, Köln, all of Germany

[73] Assignee: Bayer Aktiengesellschaft, Leverkusen, Germany

[21] Appl. No.: 09/180,972

[22] PCT Filed: May 12, 1997

[86] PCT No.: PCT/EP97/02409

§ 371 Date: Nov. 17, 1998

§ 102(e) Date: Nov. 17, 1998

[87] PCT Pub. No.: WO97/44311

PCT Pub. Date: Nov. 27, 1997

[30] Foreign Application Priority Data

May 22, 1996 [DE] Germany .................... 196 20 589

[51] Int. Cl.$^7$ .................................................. C07C 209/00
[52] U.S. Cl. ............................................................ 564/418
[58] Field of Search ................................................ 564/418

[56] References Cited

U.S. PATENT DOCUMENTS 5,072,053 12/1991 Blank et al. .
5,414,130 5/1995 Lysenko et al. .
5,574,188 11/1996 Behre et al. ............................ 564/418

OTHER PUBLICATIONS

Macromolecules (Nov. 17, 1981) p. 915.

*Primary Examiner*—Paul J. Killos
*Attorney, Agent, or Firm*—Joseph C. Gil; Diderico van Eyl

[57] ABSTRACT

The invention concerns 4,6-diamino-resorcinol which is prepared in the form of its dihydrochloride by catalytic hydrogenation of 1,3-benzyloxy-4,6-dinitrobenzene on a noble metal contact in a two-phase mixture of dilute aqueous hydrochloric acid and an organic solvent which is not miscible with dilute aqueous hydrochloric acid. This process is carried out at a pressure of between 1 and 200 bar and a temperature of between 0 and 200° C.

18 Claims, No Drawings

PROCESS FOR PREPARING 4,6-DIAMINO-RESORCINOL DIHYDROCHLORIDE

FIELD OF THE INVENTION

The present invention relates to a process for preparing 4,6-diamino-resorcinol dihydrochloride from 1,3-dichlorobenzene by dinitration to 1,3-dichloro-4,6-dinitrobenzene, subsequent reaction with sodium benzylate to 1,3-dibenzyloxy-4,6-dinitrobenzene and catalytic hydrogenation.

BACKGROUND OF THE INVENTION 4,6-Diamino-resorcinol dihydrochloride is an important building block for plastics, in particular for polybenzoxazoles (Macromolecules 1981, 915).

EP 0,402,688 describes the synthesis of 4,6-diamino-resorcinol from 1,3-dichloro-4,6-dinitrobenzene by reaction with sodium benzylate to give 1,3-dibenzyloxy-4,6-dinitrobenzene and subsequent catalytic hydrogenation. A disadvantage of the process described is the indicated way of carrying out the heterogeneous catalytic hydrogenation of 1,3-dibenzyloxy-4,6-dinitrobenzene on a Pd/activated carbon catalyst as a batch hydrogenation which, in the form described, does not permit economical recycling of the expensive noble metal catalyst. A further disadvantage is the unsatisfactory product quality, caused by the way, as described, of carrying out the heterogeneous batch hydrogenation, and the low stability of 4,6-diamino-resorcinol in the free form, in particular in water-containing solvents. A further disadvantage is the low solubility of free 4,6-diamino-resorcinol in organic solvents, which leads to an uneconomically large dilution during the operation of the catalytic hydrogenation and the isolation of the product.

It has now been found that 4,6-diamino-resorcinol dihydrochloride can be prepared from 1,3-dibenzyloxy-1,4-dinitrobenzene by reacting 1,3-dibenzyloxy-4,6-dinitrobenzene on a noble metal catalyst in a two-phase mixture of dilute aqueous hydrochloric acid and an organic solvent, which is immiscible or miscible only to a limited extent with dilute aqueous hydrochloric acid, at optionally elevated pressure and normal or elevated temperature by a catalytic hydrogenation, preferably a catalytic pump hydrogenation, to give 4,6-diamino-resorcinol dihydrochloride.

SUMMARY OF THE INVENTION

The invention therefore relates to a process for preparing 4,6-diamino-resorcinol dihyrochloride from 1,3-dibenzyloxy-4,6-dinitrobenzene, which comprises catalytically hydrogenating 1,3-dibenzyloxy-4,6-dinitrobenzene on a noble metal catalyst with hydrogen in a two-phase mixture of dilute aqueous hydrochloric acid and an organic solvent, which is immiscible or miscible only to a limited extent with dilute aqueous hydrochloric acid, at normal or elevated pressure and normal or elevated temperature.

DETAILED DESCRIPTION OF THE INVENTION

In the process according to the invention, for example 1,3-dibenzyloxy-4,6-dinitrobenzene can be employed which is prepared according to EP 0,402,688 from 1,3-dichloro-4,6-dinitrobenzene by reaction with sodium benzylate.

In a highly economical embodiment, pure 1,3-dibenzyloxy-4,6-dinitrobenzene can be obtained from 1,3-dichlorobenzene by a) reacting 1,3-dichlorobenzene in a first step in anhydrous sulfuric acid, containing 0 to 10% by weight of free $SO_3$, with a mixed acid, containing nitric acid, sulfuric acid and 0.7 to 1.5 mol, preferably 0.8 to 1.2 mol, particularly preferably 0.9 to 1.1 mol, of $SO_3$ per mol of nitric acid, in a temperature range from 0 to 40° C., the $HNO_3$/1,3-dichlorobenzene ratio being 2 to 3, and b) reacting in a second step the resulting 1,3-dichloro-4,6/2,4-dinitrobenzene isomer mixtures, which contain 0.1 to 60% of 1,3-dichloro-2,4-dinitrobenzene relative to the total weight of the isomer mixture, with 2 to 5 mol of benzyl alcohol and 2 to 5 equivalents of a strong base in the presence of an inert solvent, this being operated stepwise, initially in the temperature range from −15 to +15° C. and then in the temperature range from 20 to 40° C.

Step a) can be carried out in two different variants.

Variant 1:

1,3-Dichlorobenzene is first added dropwise to initially introduced anhydrous sulfuric acid containing 0 to 10% by weight of free $SO_3$, and the mixed acid containing nitric acid, sulfuric acid and at least 0.7 mol of $SO_3$ per mol of nitric acid is then metered in. The metering times for 1,3-dichlorobenzene are 5 minutes to 5 hours, and those for the mixed acid are 15 minutes to 10 hours and depend essentially on the reaction temperature and on the effectiveness of the cooling equipment used and on the batch size. Preferred metering times are 15 to 60 minutes for 1,3-dichlorobenzene and 1 to 3 hours for the mixed acid.

Variant 2:

1,3-Dichlorobenzene and the mixed acid containing nitric acid, sulfuric acid and at least 0.7 mol of $SO_3$ per mol of nitric acid are simultaneously metered into initially introduced anhydrous sulfuric acid containing 0 to 10% by weight of free $SO_3$. In this preferred variant, the time for simultaneous metering is 15 minutes to 10 hours, preferably 30 minutes to 3 hours, and depends on the reaction temperature and the effectiveness of the cooling equipment used and also on the batch size. In this preferred variant, the formation of 1,3-dichlorobenzenesulfonic acids is virtually completely avoided, especially if sulfuric acid containing 0 to 10% by weight of free $SO_3$ is initially introduced.

The temperature of step a) is in the range from 0 to 40° C., preferably 10 to 30° C., especially 15 to 25° C.

The nitration mixtures obtained are worked up in a form known per se, for example by discharging onto water or an ice/water mixture, filtration and washing with water.

It is essential for carrying out the process in step b) that technical isomer mixtures, obtained in step a), of 1,3-dichloro-4,6/2,4-dinitrobenzene are reacted with at least 2 mol of benzyl alcohol and at least 2 equivalents of a strong base, optionally in the presence of an inert solvent. These isomer mixtures contain in general 0.1 to 60% of 1,3-dichloro-2,4-dinitrobenzene, relative to the total weight of the mixture (remainder: 4,6-isomer). Mixtures with 5 to 25% of 1,3-dichloro-2,4-dinitrobenzene are preferably employed. A mixture of 8 to 15% of 1,3-dichloro-2,4-dinitrobenzene and 85 to 92% of- 1,3-dichloro-4,6-dinitrobenzene are very particularly preferred.

The 1,3-dichloro-4,6/2,4-dinitrobenzene isomer mixture is reacted with 2 to 5 mol, preferably 2 to 3 mol, of benzyl alcohol and with 2 to 5 equivalents of a strong base. The strong bases used are one or more metals from the group of the alkali metals, such as lithium, sodium, potassium, rubidium or cesium, preferably sodium or potassium, of the alkaline earth metals such as magnesium, calcium, strontium or barium, preferably magnesium or calcium, the alkali metal hydroxides such as lithium hydroxide, sodium hydroxide, potassium hydroxide, rubidium hydroxide or cesium hydroxide, preferably sodium hydroxide or potassium hydroxide, the alkaline earth metal hydroxides such as magnesium hydroxide, calcium hydroxide, strontium hydroxide or barium hydroxide, preferably magnesium hydroxide or calcium hydroxide, the alkali metal carbonates such as lithium carbonate, sodium carbonate, potassium carbonate, rubidium carbonate or cesium carbonate, preferably sodium carbonate or potassium carbonate, and the alkaline earth metal carbonates such as magnesium carbonate, calcium carbonate, strontium carbonate or barium carbonate, preferably magnesium carbonate or calcium carbonate. In a preferred manner, a strong base from the group of the alkali metals, the alkali metal hydroxides and alkali metal carbonates, and in a particularly preferred manner from the group sodium metal, sodium hydroxide and sodium carbonate are employed. Equally, the benzyl alcohol and the base can also be employed in the form of the preformed alcoholate.

The temperature-staged reaction of step b) is carried out in the first stage in the temperature range from −15 to +15° C., preferably 0 to 15° C., especially 5 to 15° C., and in the second reaction stage in a temperature range from 20 to 40° C., preferably 25 to 35° C.

The inert solvent used can be an aliphatic, aromatic or alkylaromatic hydrocarbon, a halogenated aromatic hydrocarbon or additional benzyl alcohol beyond the said 2 to 5 mol. Examples of such solvents are: pentane, hexane, heptane, octane, decane, dodecane and higher straight-chain or branched aliphatic hydrocarbons as well as mixtures thereof such as ligroin or petroleum ether, benzene, toluene, ethylbenzene, chlorobenzene, bromobenzene, dichlorobenzene, dibromobenzene, chlorotoluene, dichlorotoluene or cyclohexane. Of course, mixtures of several of the said solvents can also be employed.

In a preferred embodiment, benzyl alcohol is employed simultaneously as reactant and solvent. In this case, benzyl alcohol is employed in a quantity of from 3 to 20 parts by weight, preferably 5 to 15 parts by weight, relative to 1 part by weight of dichloro-dinitrobenzene. Of course, the benzyl alcohol can also be used as a mixture with the said inert solvents.

The reaction is independent of the reaction pressure and is therefore expediently carried out at normal pressure. An elevated pressure could be appropriate whenever a low-boiling solvent is used. In this case operation under the automatically established autogenous pressure is preferred. Reduced pressure is advantageous whenever the temperature-staged reaction is to be carried out in the first and/or second stage at a constant boiling temperature under reflux.

The temperature-staged reaction of dichloro-dinitrobenzene with benzyl alcohol in the presence of the said base takes in the first stage at a reaction temperature of from 5 to 15° C. in general reaction times from 15 minutes to 3 hours and in the second stage at a reaction temperature of from 25 to 35° C. in general reaction times from 30 minutes to 6 hours, and it gives high yields exceeding 90%.

The reaction product is sparingly soluble in the reaction medium and can therefore be isolated by simple filtration. The inorganic by-products (for example alkali metal chloride and/or alkaline earth metal chlorides) can then be removed by slurrying in water and repeated filtration.

It is also possible, however, to employ another pure 1,3-dibenzyloxy-4,6-dinitrobenzene, which was prepared in any desired manner in the process according to the invention.

An essential point for carrying out the process according to the invention is that the 1,3-dibenzyloxy-4,6-dinitrobenzene is reacted in a two-phase mixture in dilute aqueous hydrochloric acid and an organic solvent, which is immiscible or miscible only to a limited extent with dilute aqueous hydrochloric acid, at normal or elevated pressure and normal or elevated temperature by catalytic hydrogenation, preferably catalytic pump hydrogenation, to give 4,6-diamino-resorcinol dihydrochloride. In a preferred embodiment, a solution of the suspension of 1,3-dibenzyloxy-4,6-dinitrobenzene in an organic solvent is pumped under hydrogenation conditions into a hydrogenation autoclave, into which a suspension of the noble metal catalyst in dilute aqueous hydrochloric acid or an aqueous solution of 4,6-diamino-resorcinol dihydrochloride containing hydrochloric acid has been introduced beforehand under $H_2$ pressure.

During the catalytic hydrogenation of 1,3-dibenzyloxy-4,6-dinitrobenzene in the two-phase mixture of dilute hydrochloric acid and an organic solvent, which is immiscible or miscible only to a limited extent with dilute aqueous hydrochloric acid, a reduction of the nitro groups to the amino groups and an elimination of the benzyl groups with the formation of toluene and also a stabilization of the diamino-resorcinol, which is extremely sensitive to oxidation, in the form of the dihydrochloride take place. The preferred catalysts are platinum metals, such as palladium, platinum, rhodium or ruthenium, preferably palladium or platinum, in a quantity from 0.1 to 10% by weight, relative to the total quantity of catalyst, on a suitable support which is stable towards aqueous hydrochloric acid. Suitable supports are activated carbon, $SiO_2$, and others known to those skilled in the art. A palladium/activated carbon catalyst is very particularly preferably employed. The platinum metal-support catalyst is employed in a quantity of 0.1 to 10% by weight, calculated as platinum metal, preferably 0.2 to 2% by weight, relative to the weight of 1,3-dibenzyloxy-4,6-dinitrobenzene. The hydrogenation is carried out at an $H_2$ pressure from 1 to 200 bar, preferably 5 to 50 bar, especially 10 to 30 bar, and in the temperature range from 0 to 200° C., preferably 20 to 150° C., especially 40 to 120° C.

In the hydrogenation, which can also be carried out without pressure, the hydrogen can be replaced by suitable $H_2$-releasing substances, for example hydrazine, hydrazine hydrate, hydrazinium salts, formic acid, formates or several of these.

The concentration and quantity of the dilute aqueous hydrochloric acid, which is initially introduced into the hydrogenation autoclave, are expediently selected in the process according to the invention in such a way that the 4,6-diamino-resorcinol dihydrochloride formed is completely dissolved in the aqueous phase at the selected reaction temperature, and these are in general 0.1 to 20% by weight, preferably 1 to 15% by weight, particularly preferably from 3 to 12% by weight, and 1 to 20 g per g of 1,3-dibenzyloxy-4,6-dinitrobenzene employed, preferably 3 to 10 g/g.

The organic solvent, which is immiscible with dilute aqueous hydrochloric acid, employed for the hydrogenation can be a suitable alcohol, an ether, an aromatic or alkylaromatic hydrocarbon, a suitable organic acid or a mixture of several of these. Examples of such liquid reaction media are propanol, isopropyl alcohol, butanol, isobutanol, methyl tert-butyl ether, benzene, toluene, xylene, propionic acid or a mixture of several of these. It is essential, however, that the organic solvent, which is immiscible or miscible only to a limited extent with dilute aqueous hydrochloric acid, has a good solubility for hydrogen and a good wettability of the preferably used palladium/activated carbon catalyst. For the preferred catalytic pump hydrogenation, it is additionally essential that the organic solvent, which is immiscible or miscible only to a limited extent with dilute aqueous hydrochloric acid, has an adequate solubility for the 1,3-dibenzyloxy-4,6-dinitrobenzene, in order to enable solutions of 1,3-dibenzyloxy-4,6-dinitrobenzene to be pumped in portions or steadily into the hydrogenation autoclave in a particularly economical manner. Preferably, aromatic or alkylaromatic hydrocarbons such as benzene, toluene or xylene are employed as the organic solvent immiscible with dilute aqueous hydrochloric acid. Very particularly preferably, toluene is employed, which is formed anyway by elimination of the benzyl groups from the 1,3-dibenzyloxy-4,6-dinitrobenzene, which leads to particularly economical work-up of the two-phase reaction mixture from the hydrogenation by simple phase separation and re-use of the toluene without purification by distillation. The total solvent, which is immiscible or miscible only to a limited extent with dilute aqueous hydrochloric acid, for the hydrogenation is employed in a quantity from 0.5 to 50 parts by weight, preferably 1 to 10 parts by weight, relative to 1 part by weight of 1,3-dibenzyloxy-4,6-dinitrobenzene. Of course, a part of the organic solvent can also already be initially introduced into the hydrogenation autoclave together with the dilute, aqueous hydrochloric acid.

In detail, the process according to the invention is carried out, for example, as follows: a suspension of Pd (5%)/activated carbon catalyst in 1 to 30% by weight hydrochloric acid is initially introduced into a hydrogenation autoclave of a material which is resistant to aqueous hydrochloric acid. Under preferred hydrogenation conditions (60 to 80° C.; 10 to 20 bar $H_2$), a 10 to 80% by weight solution or suspension of 1,3-dibenzyloxy-4,6-dinitrobenzene in toluene is pumped in within the course of 30 to 90 minutes, the concentration of 1,3-dibenzyloxy-4,6-dinitrobenzene, relative to the total quantity of toluene and aqueous hydrochloric acid, being 5 to 20% by weight and the 1,3-dibenzyloxy-4,6-dinitrobenzene/palladium weight ratio being, for example, 85:1. After the absorption of hydrogen has ceased, the stirring of the reaction mixture is continued, for example for 60 minutes, at 60 to 80° C. and 10 to 20 bar $H_2$, the stirrer is stopped and about 66% of the two-phase reaction mixture of toluene and aqueous 4,6-diamino-resorcinol dihydrochloride solution containing hydrochloric acid is forced out of the hydrogenation autoclave by means of nitrogen through a riser consisting of a corrosion-resistant material and provided with a frit into a receiver. After the organic solvent (toluene) has been separated off by simple phase separation, the stable 4,6-diaminoresorcinol dihydrochloride can be isolated from the resulting aqueous solution containing hydrochloric acid, if appropriate after stripping of toluene and clarification from activated carbon, in the usual manner, for example by concentrating the aqueous solution and/or by precipitation with concentrated hydrochloric acid and/or by introducing gaseous HCl and/or, if appropriate, by salting out, for example with NaCl, or in any desired manner known to those skilled in the art, if appropriate after previous addition of a stabilizer, for example $SnCl_2$. In the same way, several hydrogenations can be carried out successively with the Pd (5%)/activated carbon catalyst employed without a decrease in the catalyst activity, which leads to a very low catalyst consumption.

It must be regarded as surprising that, by the process according to the invention, in particular in the preferred catalytic pump hydrogenation, a number of hydrogenations can be carried out one after the other without a decrease in catalyst activity, and that diamino-resorcinol dihydrochloride can be obtained as a colorless product in a particularly economical manner in a very high yield and excellent quality without further purification.

The process according to the invention can be carried out discontinuously in the manner described, for example as pump hydrogenation, or continuously, for example in loop reactors.

The invention is further described in the following illustrative examples.

EXAMPLE 1

A suspension of 25 g of moist Pd (5%)/activated carbon catalyst (20 g dry; 1 g of Pd) in 770 g of 5.5% by weight of aqueous hydrochloric acid was initially introduced into an enamelled 3 l hydrogenation autoclave. Under hydrogenation conditions, 1140 g of a 10% by weight suspension of 1,3-dibenzyloxy-4,6-dinitrobenzene in toluene (0.3 mol) was pumped at 80° C. and 10 to 20 bar $H_2$ in the course of about 30 minutes. Stirring of the reaction mixture was continued for about 1 hour at 80° C. and 10 to 20 bar $H_2$ until the hydrogen absorption ceased, the stirrer was stopped and about 1275 g (66%) of the two-phase reaction mixture of toluene and aqueous 4,6-diaminoresorcinol dihydrochloride solution containing hydrochloric acid were forced out of the hydrogenation autoclave by means of nitrogen through a riser, provided with a frit of sintered metal, into a receiver. After about 720 g of colorless toluene had been separated off by simple phase separation (upper phase), about 555 g of a yellow aqueous 4,6-diamino-resorcinol dihydrochloride solution containing hydrochloric acid were obtained. After small quantities of toluene had been separated off by incipient stripping of the aqueous solution and, if appropriate, clarification from activated carbon, if appropriate after addition of small quantities of $SnCl_2.2H_2O$, the 4,6-diamino-resorcinol dihydrochloride was precipitated by addition of about 555 g of 37% by weight of hydrochloric acid at 20 to 60° C., the resulting suspension was cooled to room temperature (20° C.) by stirring, and the very easily filtered product was isolated via a suction filter of sintered glass and dried in vacuo (100 mbar) at 20 to 60° C.

In the same manner, first a further 480 g of 6% by weight aqueous hydrochloric acid and subsequently 760 g of a 10% by weight suspension of 1,3-dibenzyloxy-4,6-dinitrobenzene in toluene (0.3 mol) were pumped at 80° C. and 10 to 20 bar $H_2$ in the course of about 30 minutes into the suspension, remaining in the hydrogenation autoclave, of the Pd (5%)/activated carbon catalyst and about 635 g of a two-phase mixture of toluene and aqueous 4,6-diamino-resorcinol dihydrochloride solution containing hydrochloric acid, and hydrogenated without a decrease in catalyst activity. About 10 hydrogenations in total were carried out one after the other in this manner, with the catalyst being recycled 9 times.

A total of 427 g of dry 4,6-diamino-resorcinol dihydrochloride was obtained.

According to HPLC (high performance liquid chromatography), the 1,3-dibenzyloxy-4,6-dinitrobenzene employed was fully converted and the isolated 4,6-diaminoresorcinol dihydrochloride was virtually a single compound according to chromatography. According to $^1$HNMR, the isolated products did not contain any benzyl groups.

Content (from chlorine) MW 213 99.7% by weight
Content (from nitrogen) MW 213 99.7% by weight Content (from carbon) MW 213 99.5% by weight
Content (from HPLC) MW 213 99.1% by weight
The yield of 4,6-diamino-resorcinol amounted to 95% of theory (from carbon), relative to 1,3-dibenzyloxy-4,6-dinitrobenzene employed.

The pure 1,3-dibenzyloxy-4,6-dinitrobenzene employed in the process according to the invention was preferably prepared in the following way:

Stage a): Technical 1,3-dichloro-4,6/2,4-dinitrobenzene mixture:

700 g of sulfuric acid monohydrate (7.14 mol) were initially introduced into a multineck-flask stirring apparatus with internal thermometer and 2 metering dropping funnels for 1,3-dichlorobenzene and mixed acid. With stirring and cooling with ice, 147 g of 99.4% 1,3-dichlorobenzene (0.99 mol) and 506 g of mixed acid (2.20 mol of $HNO_3$) were simultaneously metered in at 20° C. in the course of 1 hour, the crystallization of the nitration product starting after about 30 minutes. The reaction mixture was stirred for a further 4 hours at 20° C. The reaction mixture was transferred with stirring in the course of about 30 minutes into a receiver with 3640 g of ice/water mixture up to a maximum temperature of 20° C. The resulting product suspension was stirred for a further 1 hour at 20° C., the very easily filtered reaction product was isolated via a sintered-glass suction filter, washed acid-free with a total of about 3750 g of water and dried in vacuo at 40° C.

226 g of dry 1,3-dichloro-4,6-dinitrobenzene were obtained.

The content of the isolated product determined by GC was:
89.7% by weight of 1,3-dichloro-4,6-dinitrobenzene
10.1% by weight of 1,3-dichloro-2,4-dinitrobenzene
0.1% by weight of 1,3-dichloro-2-nitrobenzene
0.1% by weight of 1,3-dichloro-4-nitrobenzene
The yield of 1,3-dichloro-4,6-dinitrobenzene in the form of 4,6/2,4-dinitro mixture was 86.4% of theory, relative to 1,3-dichlorobenzene employed.

The mixed acid was prepared as follows:
141.4 g=2.20 mol of 98% $HNO_3$ were initially introduced. With ice-cooling and stirring, 365 g of oleum 65 (3.0 mol of $SO_3$; 1.3 mol of $H_2SO_4$) were added dropwise in the course of several hours up to a maximum temperature of 35° C.

Stage b): 1 3-Dibenzyloxy-4,6-dinitrobenzene:

1560 g of benzyl alcohol were initially introduced into a multineck-flask stirring apparatus with internal thermometer and a solids inlet. While passing through dry nitrogen and cooling with ice, 74 g of ground NaOH (1.85 mol) were introduced in the course of about 15 minutes up to a maximum temperature of 25° C. Stirring of the reaction mixture was continued for about 12 hours at room temperature (20° C.) until dissolution was complete. 183 g of 1,3-dichloro-4,6/2,4-dinitrobenzene isomer mixture (0.685 mol of 1,3-dichloro-4,6-dinitrobenzene, 0.085 mol of 1,3-dichloro-2,4-dinitrobenzene) were introduced in the course of about 30 minutes at 10° C. into the slightly cloudy reaction solution, having a yellowish color, while passing through dry nitrogen and cooling with ice/NaCl. The resulting light yellow suspension was stirred at 10° C. for a further 30 minutes, warmed to 30° C. and stirred at this temperature for about a further 3 hours. The easily filtered product mixture of 1,3-dibenzyloxy-4,6-dinitrobenzene and NaCl was isolated at 30° C. through a sintered glass suction filter and sucked thoroughly dry in order to remove the benzyl alcohol mother liquor. The isolated crude product was introduced at 20° C. into a receiver with 2500 g of water, the resulting slurry was stirred for about 1 hour at 20° C. until the NaCl was completely dissolved, the purified, virtually colorless product was filtered again, washed with about 5000 g of water in several portions in order to remove benzyl alcohol completely and, if appropriate, dried at 60° C. under a reduced pressure.

237 g of dry pure product were obtained.

The content of the isolated product, determined by HPLC, was:
Content (titanium reduction) MW 380 HPLC 99.8% by weight
1,3-Dibenzyloxy-4,6-dinitrobenzene 99.1% by weight
1-Benzyloxy-3-chloro-4,6-dinitrobenzene 0.6% by weight
1,3-Dibenzyloxy-2,4-dinitrobenzene <0.1% by weight
The yield of 1,3-dibenzyloxy-4,6-dinitrobenzene was 91.0% of theory, relative to 1,3-dichloro-4,6-dinitrobenzene employed in the form of the 1,3-dichloro-4,6/2,4-dinitrobenzene mixture.

The benzaldehyde content of the benzyl alcohol mother liquor was 0.5% according to GC.

What is claimed is:

1. A process for preparing 4,6-diamino-resorcinol dihydrochloride from 1,3-dibenzyloxy-4,6-dinitrobenzene, which comprises catalytically hydrogenating 1,3-dibenzyloxy-4,6-dinitrobenzene on a noble metal catalyst with hydrogen in a two-phase mixture of dilute aqueous hydrochloric acid with an organic solvent, which is immiscible or miscible only to a limited extent with dilute aqueous hydrochloric acid, at 1 to 200 bar and 0 to 200° C.

2. The process as claimed in claim 1, wherein the organic solvent immiscible with dilute aqueous hydrochloric acid is employed in a quantity of 0.5 to 50 parts by weight, relative to 1 part by weight of 1,3-dibenzyloxy-4,6-dinitrobenzene.

3. The process as claimed in claim 1, wherein aromatic or alkylaromatic hydrocarbons, are employed as the organic solvent immiscible with dilute aqueous hydrochloric acid.

4. The process as claimed in claim 1, wherein the catalyst employed is a platinum metal, on a support which is stable towards aqueous hydrochloric acid.

5. The process as claimed in claim 1, wherein the catalyst is employed in a quantity of 0.1 to 10% by weight, calculated as platinum metal, relative to the weight of 1,3-dibenzyloxy-4,6-dinitrobenzene.

6. The process as claimed in claim 1, wherein the catalyst employed is palladium on activated carbon.

7. The process as claimed in claim 1, wherein the hydrogenation is carried out at an $H_2$ pressure of 5 to 50 bar, and in a temperature range from 20 to 150° C.

8. The process as claimed in claim 1, wherein, in the case of unpressurized hydrogenation, the hydrogen is replaced by an $H_2$-releasing substance.

9. The process as claimed in claim 1, wherein the hydrogenation is carried out in the form of pump hydrogenation.

10. The process of claim 1, wherein the organic solvent immiscible with dilute aqueous hydrochloric acid is employed in a quantity of 1 to 10 parts by weight, relative to 1 part by weight of 1,3-dibenzyloxy-4,6-dinitrobenzene.

11. The process of claim 1, wherein the organic solvent used comprises toluene.

12. The process of claim 1, wherein the catalyst employed comprises a palladium catalyst.

13. The process of claim 1, wherein the catalyst is employed in a quantity of 0.2 to 2% by weight, relative to the weight of 1,3-dibenzyloxy-4,6-dinitrobenzene.

14. The process of claim 1, wherein the hydrogenation is carried out at a temperature ranging from 40 to 120° C.

15. The process of claim 1, wherein the hydrogenation is carried out at an $H_2$ pressure of 10 to 30 bar at a temperature ranging from 20 to 150° C.

16. The process of claim 15, wherein the hydrogenation is carried out at a temperature ranging from about 40 to 120° C.

17. The process of claim 8, wherein the $H_2$-releasing substance comprises a component selected from the group consisting of hydrazine, hydrazine hydrate, hydrazinium salts, formic acid, formates, and mixtures thereof.

18. The process of claim 1, wherein the 4,6-diamino-resorcinol dihydrochloride is prepared at a yield of about 95%.

* * * * *